(12) United States Patent
Currie

(10) Patent No.: US 10,251,787 B2
(45) Date of Patent: Apr. 9, 2019

(54) ILLUMINATED WELDING HELMET SYSTEM

(71) Applicant: Eric Currie, Warren, OH (US)

(72) Inventor: Eric Currie, Warren, OH (US)

( * ) Notice: Subject to any disclaimer, the term of this patent is extended or adjusted under 35 U.S.C. 154(b) by 49 days.

(21) Appl. No.: 15/468,199

(22) Filed: Mar. 24, 2017

(65) Prior Publication Data

US 2018/0271709 A1  Sep. 27, 2018

(51) Int. Cl.
*A61F 9/06* (2006.01)

(52) U.S. Cl.
CPC .................................... *A61F 9/067* (2013.01)

(58) Field of Classification Search
CPC .... A61F 9/06; A61F 9/067; F21L 4/04; F21V 23/0492
See application file for complete search history.

(56) References Cited

U.S. PATENT DOCUMENTS

| | | | |
|---|---|---|---|
| 3,227,866 A * | 1/1966 | Peters | A61F 9/06 200/61.47 |
| 4,071,912 A * | 2/1978 | Budmiger | A61F 9/067 2/8.8 |
| 4,332,004 A * | 5/1982 | Slaughter | F16P 1/06 2/10 |
| 4,670,821 A | 6/1987 | Treadway | |
| D296,832 S | 7/1988 | Bachik | |
| 5,959,705 A * | 9/1999 | Fergason | B23K 9/32 2/8.8 |
| 6,340,234 B1 * | 1/2002 | Brown, Jr. | A61F 9/06 362/105 |
| 7,150,047 B2 * | 12/2006 | Fergason | A61F 9/067 2/8.1 |
| 7,186,950 B1 | 3/2007 | Fisher | |
| 7,934,846 B1 | 5/2011 | Schwanz | |
| 8,721,103 B2 | 5/2014 | Robinson | |
| 8,990,964 B2 * | 3/2015 | Anderson | A61F 9/06 2/8.2 |
| 9,629,752 B1 * | 4/2017 | Graham | A61F 9/067 |
| 2011/0107491 A1 | 5/2011 | Sanders et al. | |

* cited by examiner

Primary Examiner — Tajash D Patel

(57) ABSTRACT

An illuminated welding helmet system for selectively illuminating a darkened area during welding operations includes a welding helmet that may be worn during welding and the welding helmet includes an auto lens. A light unit is coupled to the welding helmet and the light unit selectively emits light outwardly from the welding helmet thereby facilitating a darkened area to be visible. The light unit is in electrical communication with the auto lens. Moreover, the light unit is turned on when the auto lens does not detect light and the light unit is turned off when the auto lens detects light.

6 Claims, 4 Drawing Sheets

ILLUMINATED WELDING HELMET SYSTEM

CROSS-REFERENCE TO RELATED APPLICATIONS

Not Applicable

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC OR AS A TEXT FILE VIA THE OFFICE ELECTRONIC FILING SYSTEM

Not Applicable

STATEMENT REGARDING PRIOR DISCLOSURES BY THE INVENTOR OR JOINT INVENTOR

Not Applicable

BACKGROUND OF THE INVENTION (1) Field of the Invention (2) Description of Related Art Including Information Disclosed Under 37 CFR 1.97 and 1.98.

The disclosure and prior art relates to welding systems and more particularly pertains to a new welding system for selectively illuminating a darkened area during welding operations.

BRIEF SUMMARY OF THE INVENTION

An embodiment of the disclosure meets the needs presented above by generally comprising a welding helmet that may be worn during welding and the welding helmet includes an auto lens. A light unit is coupled to the welding helmet and the light unit selectively emits light outwardly from the welding helmet thereby facilitating a darkened area to be visible. The light unit is in electrical communication with the auto lens. Moreover, the light unit is turned on when the auto lens does not detect light and the light unit is turned off when the auto lens detects light.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF SEVERAL VIEWS OF THE DRAWING(S)

The disclosure will be better understood and objects other than those set forth above will become apparent when consideration is given to the following detailed description thereof. Such description makes reference to the annexed drawings wherein.

DETAILED DESCRIPTION OF THE INVENTION

Figure 1:
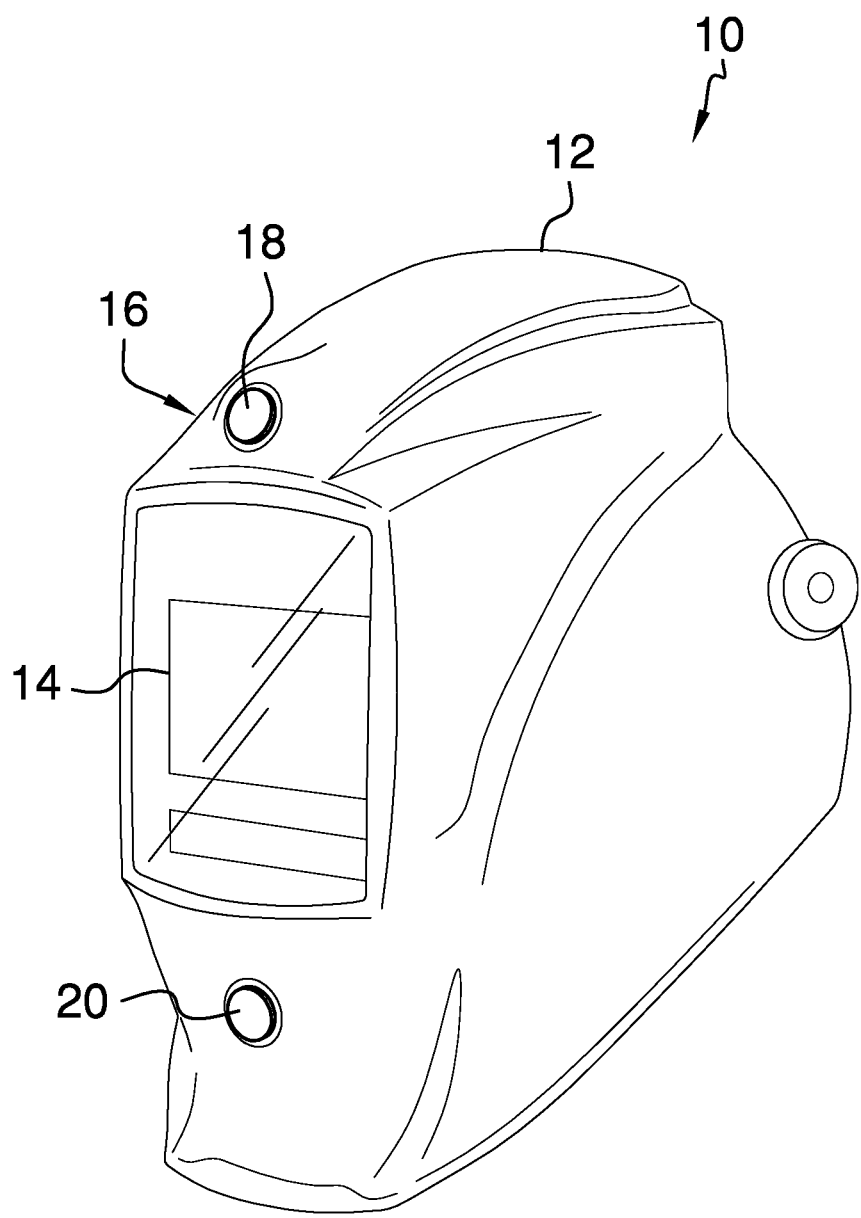
FIG. 1 is a front perspective view of an illuminated welding helmet system according to an embodiment of the disclosure.

With reference now to the drawings, and in particular to FIGS. 1 through 4 thereof, a new welding system embodying the principles and concepts of an embodiment of the disclosure and generally designated by the reference numeral 10 will be described.

As best illustrated in FIGS. 1 through 4, the illuminated welding helmet system 10 generally comprises a welding helmet 12 that may be worn during welding. The welding helmet 12 includes an auto lens 14. The auto lens 14 may be an automatically darkening welding lens of any conventional design. Moreover, the auto lens 14 darkens when the auto lens 14 detects light from a light source that exceeds a trigger intensity of light. The light source may be an electrical arc from an electric welder.

A light unit 16 is provided and the light unit 16 is coupled to the welding helmet 12. The light unit 16 emits light outwardly from the welding helmet 12 to illuminate a darkened area. In this way a user can see to accurately position a welding probe in the darkened area. The light unit 16 is in electrical communication with the auto lens 14. The light unit 16 is turned on when the auto lens 14 does not detect light and the light unit 16 is turned off when the auto lens 14 detects light.

The light unit 16 comprises a first light emitter 18 that is coupled to the welding helmet 12. The first light emitter 18 selectively emits light outwardly from the welding helmet 12. The first light emitter 18 is electrically coupled to the auto lens 14 and the first light emitter 18 may be a LED or the like. Moreover, the first light emitter 18 may emit a selected color of light. The first light emitter 18 is turned on when the auto lens 14 does not detect light and the first light emitter 18 is turned off when the auto lens 14 detects light. The first light emitter 18 may be positioned adjacent to a top side of the welding helmet 12.

A second light emitter 20 is provided and the second light emitter 20 is coupled to the welding helmet 12. The second light emitter 20 selectively emits light outwardly from the welding helmet 12. The second light emitter 20 is electrically coupled to the auto lens 14 and the second light emitter 20 may be an LED or the like. Additionally, the second light emitter 20 may emit a selected color of light. The second light emitter 20 is turned on when the auto lens 14 does not detect light and the second light emitter 20 is turned off when the auto lens 14 detects light. The second light emitter 20 may be positioned adjacent to a bottom side of the welding helmet 12.

Figure 2:
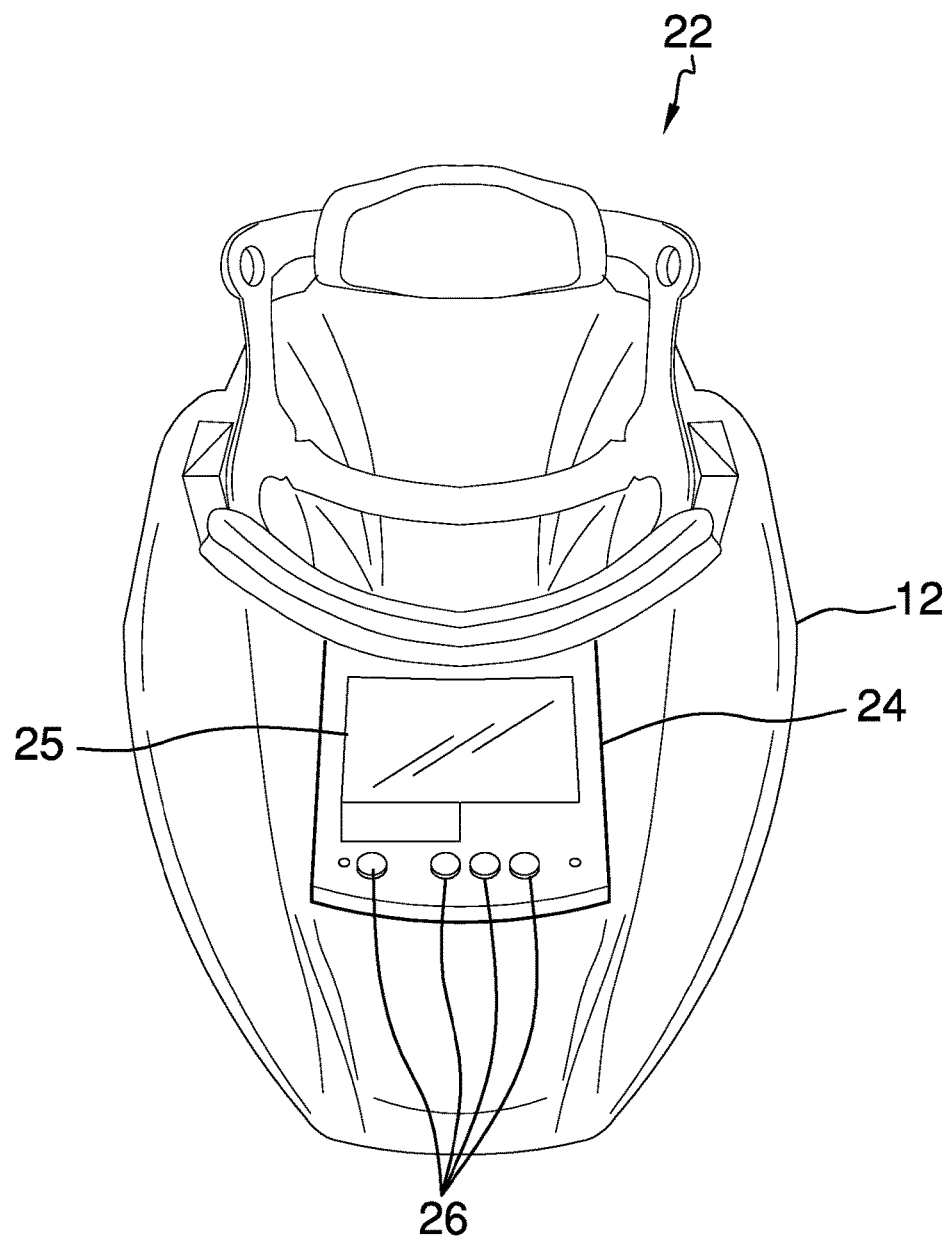
FIG. 2 is a back view of an alternative embodiment of the disclosure.
Figure 3:
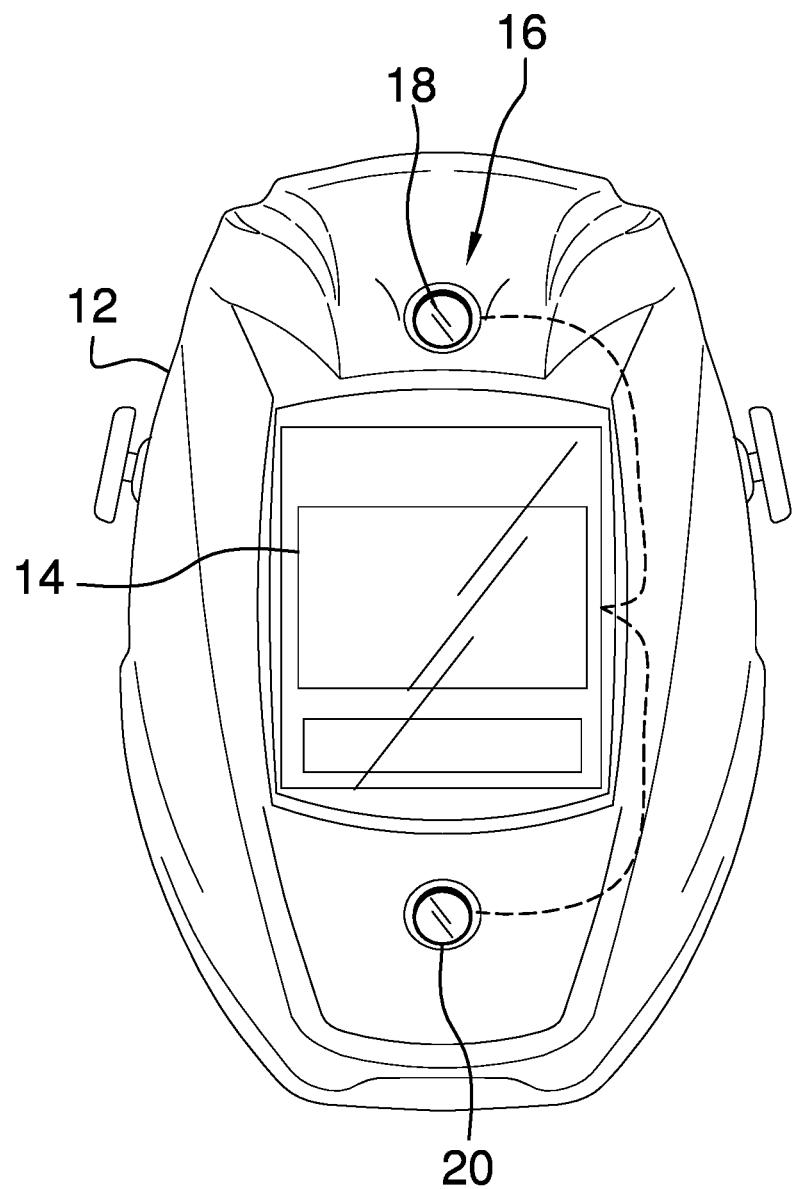
FIG. 3 is a front phantom view of an embodiment of the disclosure.
Figure 4:
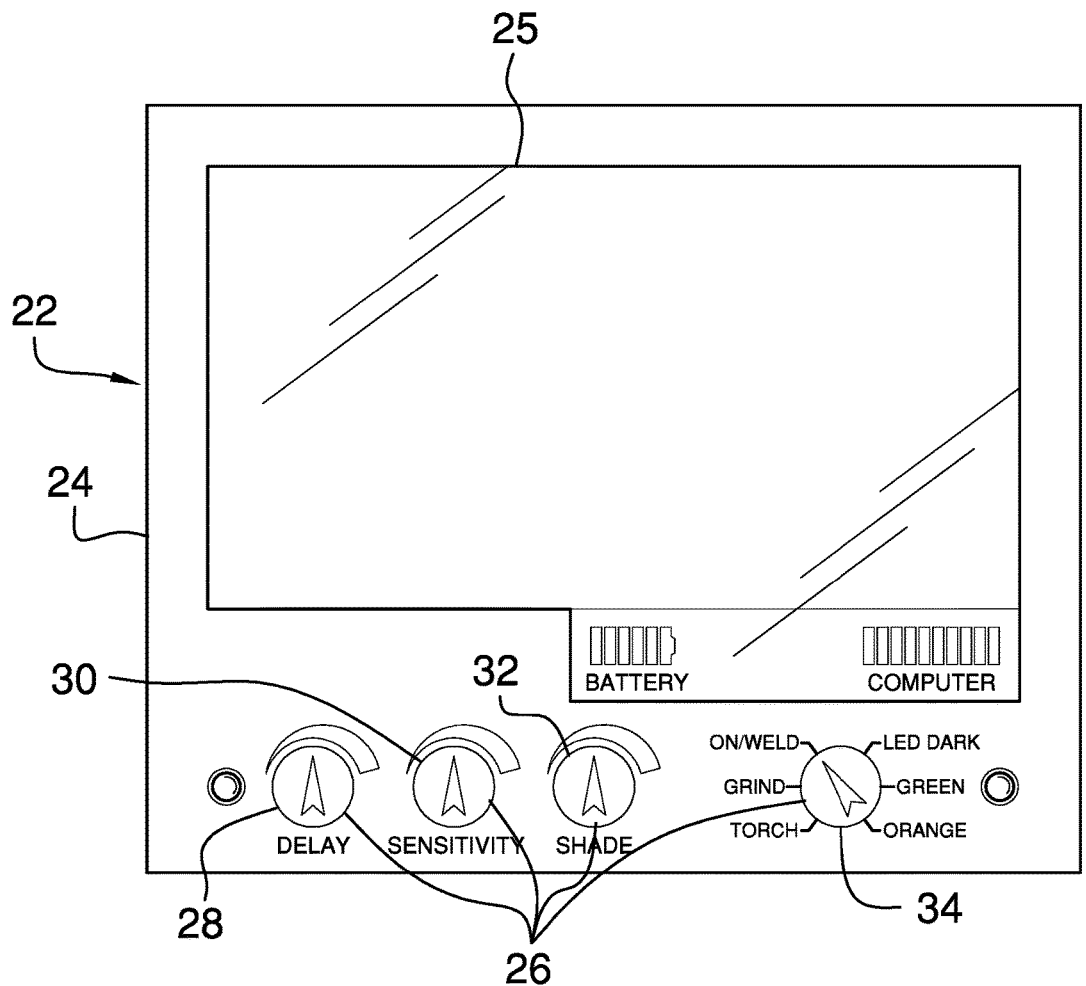
FIG. 4 is a perspective view of an alternative embodiment of the disclosure.

In an alternative embodiment 22 as shown in FIGS. 2 and 4, a control panel 24 may be provided and the control panel 24 may be positioned within the welding helmet 12. The control panel 24 may be electrically coupled to the auto lens 14, the first light emitter 18 and the second light emitter 20.

The control panel 24 may include a display 25 and a plurality of knobs 26. The display 25 may be an LED display or the like and the display 25 may display operational parameters corresponding to each of the auto lens 14, the first light emitter 18 and the second light emitter 20. The plurality of knobs 26 may include a delay knob 28, a sensitivity knob 30, a shade knob 32 and a color knob 34.

In use, the welding helmet 12 is worn during the performance of welding operations. Each of the first light emitter 18 and the second light emitter 20 are turned on when the welding helmet 12 is worn in a darkened area. In this way the darkened area is illuminated thereby facilitating the welding probe to be accurately positioned to begin welding. Each of the first light emitter 18 and the second light emitter 20 turn off when the auto lens 14 detects light from the welding probe of other source of light that exceeds the trigger sensitivity.

With respect to the above description then, it is to be realized that the optimum dimensional relationships for the parts of an embodiment enabled by the disclosure, to include variations in size, materials, shape, form, function and manner of operation, system and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be only one of the elements.

The invention claimed is:

1. An illuminated welding helmet system comprising:
   a welding helmet being configured to be worn during welding, said welding helmet including an auto lens; and
   a light unit being coupled to said welding helmet wherein said light unit is configured to emit light outwardly and forwardly from said welding helmet thereby facilitating a darkened area to be visible, said light unit being in electrical communication with said auto lens, said light unit being turned on when said auto lens does not detect light, said light unit being turned off when said auto lens detects light.

2. The system according to claim 1, wherein said light unit comprises a first light emitter being coupled to said welding helmet wherein said first light emitter is configured to emit light outwardly from said welding helmet.

3. The system according to claim 2, wherein said first light emitter is electrically coupled to said auto lens, said first light emitter being turned on when said auto lens does not detect light, said first light emitter being turned off when said auto lens detects light.

4. The system according to claim 1, further comprising a second light emitter being coupled to said welding helmet wherein said second light emitter is configured to emit light outwardly from said welding helmet.

5. The system according to claim 1, wherein said second light emitter is electrically coupled to said auto lens, said second light emitter being turned on when said auto lens does not detect light, said second light emitter being turned off when said auto lens detects light.

6. An illuminated welding helmet system comprising:
   a welding helmet being configured to be worn during welding, said welding helmet including an auto lens; and
   a light unit being coupled to said welding helmet wherein said light unit is configured to emit light outwardly and forwardly from said welding helmet thereby facilitating a darkened area to be visible, said light unit being in electrical communication with said auto lens, said light unit being turned on when said auto lens does not detect light, said light unit being turned off when said auto lens detects light, said light unit comprising:
      a first light emitter being coupled to said welding helmet wherein said first light emitter is configured to emit light outwardly from said welding helmet, said first light emitter being electrically coupled to said auto lens, said first light emitter being turned on when said auto lens does not detect light, said first light emitter being turned off when said auto lens detects light, and
      a second light emitter being coupled to said welding helmet wherein said second light emitter is configured to emit light outwardly from said welding helmet, said second light emitter being electrically coupled to said auto lens, said second light emitter being turned on when said auto lens does not detect light, said second light emitter being turned off when said auto lens detects light.

* * * * *